US011998409B2

(12) United States Patent
Oh et al.

(10) Patent No.: US 11,998,409 B2
(45) Date of Patent: Jun. 4, 2024

(54) DENTAL COMPOSITE BLANK AND METHOD FOR MANUFACTURING SAME (71) Applicant: VERICOM CO., LTD., Chuncheon-si (KR)

(72) Inventors: Myung-Hwan Oh, Seoul (KR); Jong-Ho Kang, Bucheon-si (KR); Hyun-Chul Yoo, Gunpo-si (KR); Joung-Lim Hoo, Anyang-si (KR); Yun-Ki Kim, Anyang-si (KR)

(73) Assignee: VERICOM CO., LTD., Chuncheon-si (KR)

( * ) Notice: Subject to any disclaimer, the term of this patent is extended or adjusted under 35 U.S.C. 154(b) by 1017 days.

(21) Appl. No.: 16/957,211

(22) PCT Filed: Dec. 28, 2018

(86) PCT No.: PCT/KR2018/016873
§ 371 (c)(1),
(2) Date: Jun. 23, 2020

(87) PCT Pub. No.: WO2019/132595
PCT Pub. Date: Jul. 4, 2019

(65) Prior Publication Data
US 2020/0405461 A1 Dec. 31, 2020

(30) Foreign Application Priority Data
Dec. 28, 2017 (KR) .................. 10-2017-0181939

(51) Int. Cl.
*A61C 13/08* (2006.01)
*A61C 13/00* (2006.01)
(Continued)

(52) U.S. Cl.
CPC ........ *A61C 13/081* (2013.01); *A61C 13/0022* (2013.01); *A61C 13/087* (2013.01); *A61K 6/887* (2020.01)

(58) Field of Classification Search
CPC .................. A61C 13/0022; A61C 13/0006
See application file for complete search history.

(56) References Cited

U.S. PATENT DOCUMENTS 7,255,562 B2 * 8/2007 Rusin ................. A61K 6/891
433/223
2014/0272798 A1 9/2014 McDermott et al.
(Continued)

FOREIGN PATENT DOCUMENTS

JP 2015097854 A 5/2015
KR 1020160010865 A 1/2016
(Continued)

OTHER PUBLICATIONS

International Search Report of PCT/KR2018/016873, Apr. 3, 2019, English translation.
(Continued)

*Primary Examiner* — Liam J Heincer
(74) *Attorney, Agent, or Firm* — STIP Law Group, LLC (57) ABSTRACT The present invention relates to a method of manufacturing a dental composite blank, including (a) placing a composite paste in a mold, (b) pressurizing the composite paste placed in the mold at a first pressure ($P_1$), (c) pressurizing the composite paste placed in the mold at a second pressure ($P_2$), and (d) curing the pressurized composite paste, in which each of steps (b) and (c) is performed once or multiple times, and the first pressure ($P_1$) is less than or greater than the second pressure ($P_2$). The dental composite blank and the method of manufacturing the same are effective at dispersing a non-dispersed filler and removing bubbles, thus improving mechanical properties, through repeated pressur-
(Continued)

ization at different pressures before curing the composite paste.

17 Claims, 2 Drawing Sheets

(51) Int. Cl.
*A61C 13/087* (2006.01)
*A61K 6/887* (2020.01)

(56) References Cited

U.S. PATENT DOCUMENTS

| | | | | |
|---|---|---|---|---|
| 2015/0182315 A1* | 7/2015 | Okada | A61C 13/0006 | |
| | | | 264/16 | |
| 2016/0128812 A1* | 5/2016 | Nakayama | A61C 13/08 | |
| | | | 264/19 | |
| 2017/0252136 A1* | 9/2017 | Fung | A61C 13/26 | |
| 2018/0333236 A1* | 11/2018 | Althobity | A61C 8/0001 | |
| 2020/0237487 A1* | 7/2020 | Inoue | A61C 13/082 | |
| 2020/0261196 A1* | 8/2020 | Ruppert | A61C 19/003 | |
| 2020/0268616 A1* | 8/2020 | Wang | B29B 7/90 | |
| 2020/0360120 A1* | 11/2020 | Inoue | A61C 13/0022 | |
| 2022/0079724 A1* | 3/2022 | Oh | B32B 37/10 | |

FOREIGN PATENT DOCUMENTS

| | | | |
|---|---|---|---|
| KR | 20160024334 A | * | 3/2016 |
| KR | 1020160024334 A | | 3/2016 |
| KR | 101676343 B1 | | 11/2016 |
| WO | WO2015045698 A1 | | 4/2015 |
| WO | WO2016032012 A1 | | 3/2016 |
| WO | WO2016014724 A1 | | 6/2016 |

OTHER PUBLICATIONS

Office Action from Korean Intellectual Property Office of 10-2018-0172246, Nov. 11, 2019.

* cited by examiner

DENTAL COMPOSITE BLANK AND METHOD FOR MANUFACTURING SAME

CROSS-REFERENCE TO RELATED APPLICATIONS

This application is the U.S. National Phase under 35 U.S.C. § 371 of International Application No. PCT/KR2018/016873 filed on Dec. 28, 2018, which in turn claims the benefit of Korean Application No. 10-2017-0181939, filed on Dec. 28, 2017, the disclosures of which are incorporated by reference into the present application.

TECHNICAL FIELD

The present invention relates to a dental composite blank and a method of manufacturing the same, and more particularly to a dental composite blank imparted with improved mechanical properties by repeating pressurization at different pressures before curing a dental composite paste and to a method of manufacturing the same.

BACKGROUND ART

Dental prosthetic materials used in dental prosthetics are key dental materials that are used for a very wide range of dental treatment, such as orthodontics or aesthetic dentistry, in addition to general dental procedures that fix loose teeth or repair the entire crown or a damaged area of a tooth caused by a cavity or fracturing of the tooth.

Typical dental prostheses include restorations, supplements, inlays, onlays, veneers, whole and partial crowns, bridges, implants, posts, and the like. Prostheses are manually manufactured by a dentist with expertise or are manufactured by a dental technician, who is a professional engineer skilled in dental technology.

Due to the recent development of technology, computer automation devices such as optical devices, digital devices, mechanical milling devices and CAD/CAM have significantly reduced the amount of manual labor performed by dental technicians and the period required to manufacture dental prostheses. Such computer automation devices are capable of manufacturing dental prostheses by cutting, milling, and crushing the required restoration to impart the correct shape and form thereto at a faster speed and with less labor than conventional manual methods. Dental prostheses using CAD/CAM devices typically use mill blanks, that is, solid blanks, which are the materials from which the prosthesis is cut or shaped.

A mill blank is mainly made of a material of zirconia, glass ceramics, recently introduced hybrid ceramics, etc. However, the use of zirconia and glass ceramics is time-consuming due to complicated post-processing thereof, and opposing teeth may be damaged due to the rigidity of zirconia or glass ceramics. Also, although existing hybrid ceramics are receiving attention because of the simple processing and aesthetics similar to those of natural teeth, but are not competitive for repair of posterior teeth owing to the remarkably low mechanical strength thereof compared to zirconia or glass ceramics.

U.S. Patent Application Publication No. 2014/0272798 (Sep. 18, 2014) discloses a method of manufacturing a removable denture not including a filler, and Korean Patent Application Publication No. 10-2016-0024334 (Mar. 4, 2016) discloses a dental composite blank in the form of a hollow column having a void inside.

DISCLOSURE

Technical Problem

Accordingly, the present invention has been made keeping in mind the problems encountered in the related art, and an objective of the present invention is to provide a dental composite blank, in which a non-dispersed filler is dispersed and bubbles are removed by repeating pressurization at different pressures before curing a dental composite paste, and a method of manufacturing the same.

Another objective of the present invention is to provide a dental composite blank imparted with improved mechanical properties by dispersing a non-dispersed filler and removing bubbles, and a method of manufacturing the same.

Technical Solution

An aspect of the present invention provides a method of manufacturing a dental composite blank, including (a) placing a composite paste in a mold, (b) pressurizing the composite paste placed in the mold at a first pressure $P_1$, (c) pressurizing the composite paste placed in the mold at a second pressure $P_2$, and (d) curing the pressurized composite paste, in which each of steps (b) and (c) is performed once or multiple times, and the first pressure $P_1$ is less than or greater than the second pressure $P_2$.

Here, any one of steps (b) and (c) may be performed, and then the remaining one thereof may be performed.

Steps (b) and (c) may be repeatedly performed.

Each of steps (b) and (c) may be performed 1 to 20 times, and steps (b) and (c) may be alternately performed.

Any one of the first pressure $P_1$ and the second pressure $P_2$ may be 5 to 300 MPa, and the remaining one thereof may be 1 to 10 MPa.

The difference between the first pressure $P_1$ and the second pressure $P_2$ may be 5 to 299 MPa.

Each of steps (b) and (c) may independently be performed at 10 to 59° C.

Curing may not be performed in each of steps (b) and (c).

Steps (b) and (c) may be performed in an inert gas atmosphere.

The inert gas may be nitrogen or argon.

Step (d) may be performed at a pressure of 5 to 300 MPa.

Step (d) may be performed at a temperature of 80 to 200° C.

Step (b) may be performed multiple times, and during step (b) performed multiple times, the pressure $P_1(1)$ in step (b) performed for the first time may be the same as or different from the pressure $P_1(2)$ in step (b) performed later.

Step (c) may be performed multiple times, and during step (c) performed multiple times, the pressure $P_2(1)$ in step (c) performed for the first time may be the same as or different from the pressure $P_2(2)$ in step (c) performed later.

The composite paste may include at least one unsaturated-double-bond compound selected from among a monomer containing an unsaturated double bond and an oligomer of a monomer containing an unsaturated double bond, a filler, and a polymerization initiator.

The monomer containing the unsaturated double bond may be a methacrylate (MA) monomer or an acrylate monomer.

The monomer may include at least one selected from among 2,2-bis[4-(2-hydroxy-3-methacryloxypropoxy) phenyl]propane (Bis-GMA), ethylene glycol dimethacrylate (EGDMA), ethylene glycol diacrylate (EDGA), triethylene glycol dimethacrylate (TEGDMA), triethylene glycol diacrylate (TEGDA), ethoxylated bisphenol A dimethacrylate (Bis-EMA), urethane dimethacrylate (UDMA), polyurethane diacrylate (PUDA), dipentaerythritol pentaacrylate monophosphate (PENTA), 2-hydroxyethyl methacrylate (HEMA), polyalkenoic acid, biphenyl dimethacrylate (BPDM), biphenyl diacrylate (BPDA) and glycerol phosphate dimethacrylate (GPDM).

The filler may include at least one selected from among an inorganic filler and an organic filler.

The inorganic filler may include at least one selected from among synthetic amorphous silica, crystalline silica, barium silicate, barium borosilicate, barium fluoroaluminoborosilicate, barium aluminoborosilicate, strontium silicate, strontium borosilicate, strontium aluminoborosilicate, calcium silicate, aluminosilicate, silicon nitride, titanium dioxide, calcium hydroxyapatite, zirconia and bioactive glass.

Here, synthetic amorphous silica, crystalline silica and zirconia may be in the form of particles, and the particles may have an average diameter of 0.01 to 0.1 μm.

Also, barium silicate, barium borosilicate, barium fluoroaluminoborosilicate, barium aluminoborosilicate, strontium silicate, strontium borosilicate and strontium aluminoborosilicate may be in the form of particles, and the particles may have an average diameter of 0.1 to 3 μm.

The polymerization initiator may include at least one selected from among a photopolymerization initiator and a thermal polymerization initiator.

The composite paste may include 100 parts by weight of the unsaturated-double-bond compound, 50 to 1,000 parts by weight of the filler, and 0.01 to 5 parts by weight of the polymerization initiator.

Another aspect of the present invention provides a dental composite blank manufactured by polymerizing a composite paste including 100 parts by weight of at least one unsaturated-double-bond compound selected from the group consisting of a monomer containing an unsaturated double bond and an oligomer of a monomer containing an unsaturated double bond, 50 to 1,000 parts by weight of a filler, and 0.01 to 5 parts by weight of a polymerization initiator, in which the composite blank has flexural strength of 200 to 300 MPa.

The flexural strength may be 210 to 260 MPa.

Advantageous Effects

According to the present invention, a dental composite blank and a method of manufacturing the same are effective at dispersing a non-dispersed filler and removing bubbles by repeating pressurization at different pressures before curing a dental composite paste.

In addition, a dental composite blank and a method of manufacturing the same are effective at improving mechanical properties by dispersing a non-dispersed filler and removing bubbles.

BEST MODE

The present invention may be embodied in many different forms, and should not be construed as being limited only to the embodiments set forth herein, but should be understood to cover all modifications, equivalents or alternatives falling within the ideas and technical scope of the present invention. In the description of the present invention, detailed descriptions of related known techniques incorporated herein will be omitted when the same may make the gist of the present invention unclear.

As used herein, the terms "first", "second", etc. may be used to describe various elements, but these elements are not to be construed as being limited by these terms. These terms are only used to distinguish one element from another. For example, a first element may be termed a second element, and similarly, a second element may be termed a first element, without departing from the scope of the present invention.

Further, it will be understood that when an element is referred to as being "formed" or "laminated" on another element, it can be formed or laminated so as to be directly attached to all surfaces or to one surface of the other element, or intervening elements may be present therebetween.

Unless otherwise stated, a singular expression includes a plural expression. In the present application, the terms "comprise", "include" or "have" are used to designate the presence of features, numbers, steps, operations, elements, parts, or combinations thereof described in the specification, and should be understood as not excluding the additional presence or possible presence of one or more different features, numbers, steps, operations, elements, parts, or combinations thereof.

Hereinafter, a detailed description will be given of a method of manufacturing a dental composite blank according to the present invention.

First, a composite paste is placed in a mold (step a).

Figure 1A:
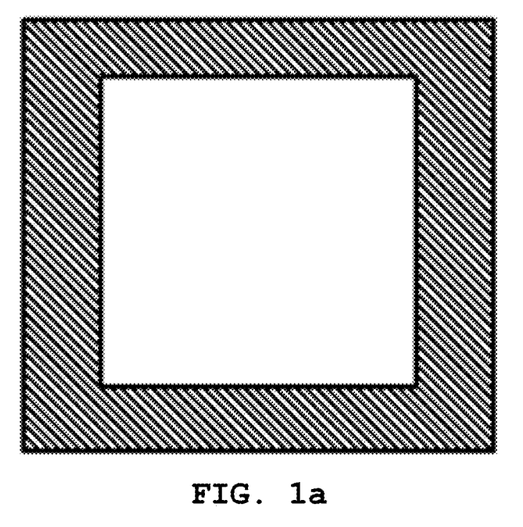
FIG. 1a is a top plan view of a mold for introducing a dental composite paste therein.
Figure 1B:
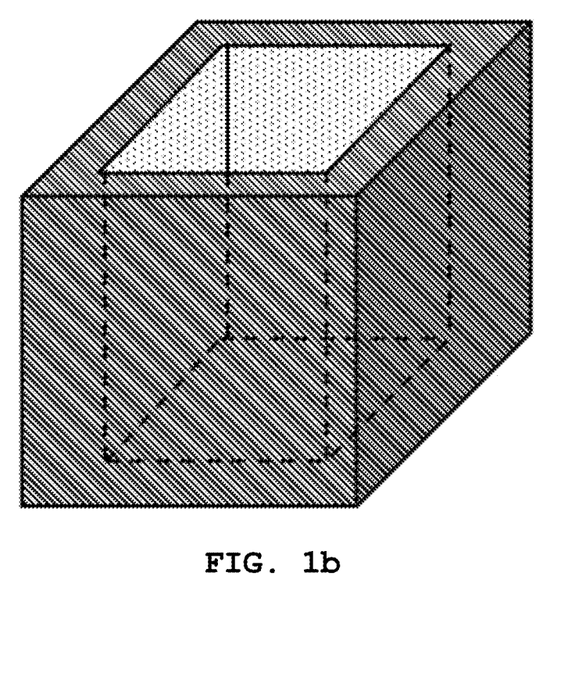
FIG. 1b is a perspective view of the mold for introducing a dental composite paste therein.

FIGS. 1a and 1b show shapes when the mold in which a dental composite paste is placed is viewed from above and from the front, respectively. The mold is provided in the form of a quadrangular prism, the inside of which is cut and the top and bottom of which are open, but when the viscosity of the dental composite paste is high, the paste does not flow even when introduced into the mold.

Also, when the viscosity of the dental composite paste is low, the paste may flow when introduced into the mold, so the bottom surface of the mold is blocked with the same material as the mold, thereby preventing the flow of the paste, and the bottom surface of the mold may be provided in a removable form in order to facilitate separation of the bottom surface after curing the dental composite paste.

The material for the mold may include polypropylene, polystyrene, polyphenylene sulfide, polytetrafluoroethylene, polyethersulfone, polyetheretherketone, polyetherimide, polycarbonate, nylon, silicone, and the like, and preferably includes nylon.

Next, the composite paste placed in the mold is pressurized at a first pressure $P_1$ (step b).

Subsequently, the composite paste placed in the mold is pressurized at a second pressure $P_2$ (step c).

Here, each of steps (b) and (c) may be performed once or multiple times.

Any one of steps (b) and (c) may be performed, and then the remaining one thereof may be performed.

Steps (b) and (c) may be performed repeatedly.

Each of steps (b) and (c) may be performed 1 to 20 times, and steps (b) and (c) may be alternately performed, and are preferably conducted 3 to 15 times. If the number of steps is less than 1, the effect of removing bubbles may become insignificant. On the other hand, if the number of steps exceeds 20, the effect of increasing strength may not be further improved, which is undesirable.

Figure 2:
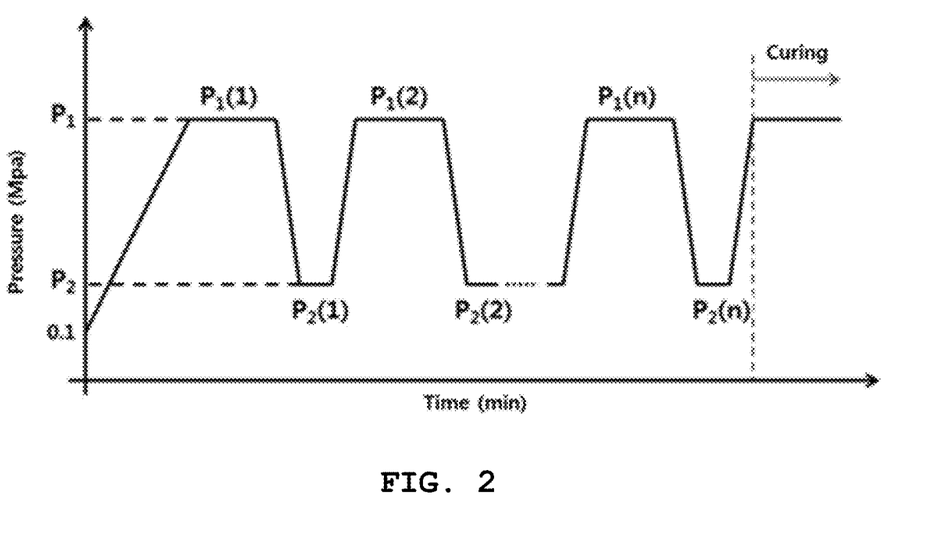
FIG. 2 is a graph showing a change in pressure in a process of manufacturing a dental composite blank according to an embodiment of the present invention.
Figure 3:
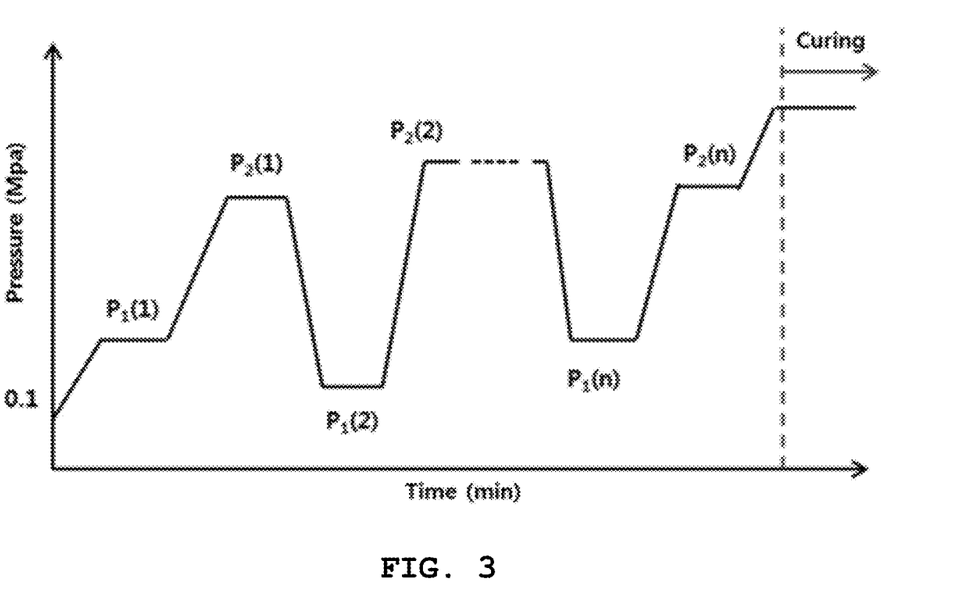
FIG. 3 is a graph showing a change in pressure in a process of manufacturing a dental composite blank according to another embodiment of the present invention.

With reference to FIGS. 2 and 3, the first pressure $P_1$ may be less than or greater than the second pressure $P_2$.

Any one of the first pressure $P_1$ and the second pressure $P_2$ may be 5 to 300 MPa, and preferably 10 to 150 MPa, and the remaining one thereof may be 1 to 10 MPa. If pressurization is conducted at a pressure less than 1 MPa, there is no effect of removing bubbles from the paste, making it impossible to increase mechanical strength. On the other hand, if pressurization is conducted at a pressure exceeding 300 MPa, the effect of increasing mechanical strength is insignificant.

A difference between the first pressure $P_1$ and the second pressure $P_2$ may be 5 to 299 MPa.

Each of steps (b) and (c) may be independently performed at 10 to 59° C. When the processing temperature falls in the range of 10 to 59° C., curing does not occur in the composite paste and flexural strength does not decrease, so mechanical properties may be maintained. However, if the temperature is lower than 10° C., the fluidity of the paste is not great and thus desired effects may not be attained. On the other hand, if the temperature is higher than 60° C., curing may occur in portions of the composite paste, undesirably lowering flexural strength.

Curing may not be performed in each of steps (b) and (c).

Steps (b) and (c) may be performed in an inert gas atmosphere, and the inert gas may be nitrogen or argon.

With reference to FIGS. 2 and 3, step (b) is performed multiple times, and during step (b) performed multiple times, the pressure $P_1(1)$ in step (b) performed for the first time may be the same as or different from the pressure $P_1(2)$ in step (b) performed later.

Step (c) is performed multiple times, and during step (c) performed multiple times, the pressure $P_2(1)$ in step (c) performed for the first time may be the same as or different from the pressure $P_2(2)$ in step (c) performed later.

Specifically, $P_1(1)$, $P_1(2)$, ..., and $P_1(n)$ are each independently the same as or different from each other, and $P_2(1)$, $P_2(2)$, ..., and $P_2(n)$ are each independently the same as or different from each other. Moreover, after performing steps up to $P_2(n)$, curing may be performed through pressurization again, or after performing steps up to $P_1(n)$, curing may be performed in the state in which the pressure is maintained.

Finally, the pressurized composite paste is cured, thus manufacturing a dental composite blank (step d).

Step (d) may be performed at a pressure of 5 to 300 MPa.

Step (d) may be performed at a temperature of 80 to 200° C.

The composite paste may include at least one unsaturated-double-bond compound selected from among a monomer containing an unsaturated double bond and an oligomer of a monomer containing an unsaturated double bond, a filler, and a polymerization initiator.

The amount of the at least one selected from among the monomer containing the unsaturated double bond and the oligomer of the monomer containing the unsaturated double bond may vary depending on the field and purpose of use. The monomer containing the unsaturated double bond and the oligomer of the monomer containing the unsaturated double bond may play an important role in determining the degree of dispersion during polymerization of the paste composition, and may be an important factor in determining wear resistance and workability.

If the total amount of the monomer and oligomer is less than 10 wt % based on the total weight of the paste composition, it is difficult to form a polymer and to perform mixing with the filler. On the other hand, if the total amount of the monomer and oligomer exceeds 40 wt % based on the total weight of the paste composition, mechanical strength may be decreased, which is undesirable. Thus, at least one selected from among the monomer containing the unsaturated double bond and the oligomer of the monomer containing the unsaturated double bond may be included in an amount of 10 to 40 wt %, and preferably 16 to 25 wt %, based on the total weight of the paste composition.

The monomer containing the unsaturated double bond may be a methacrylate (MA) monomer or an acrylate monomer, but any material may be used, so long as it is able to exhibit mechanical strength as a dental material and is polymerizable.

The monomer may include at least one selected from among 2,2-bis[4-(2-hydroxy-3-methacryloxypropoxy) phenyl]propane (Bis-GMA), ethylene glycol dimethacrylate (EGDMA), ethylene glycol diacrylate (EDGA), triethylene glycol dimethacrylate (TEGDMA), triethylene glycol diacrylate (TEGDA), ethoxylated bisphenol A dimethacrylate (Bis-EMA), urethane dimethacrylate (UDMA), polyurethane diacrylate (PUDA), dipentaerythritol pentaacrylate monophosphate (PENTA), 2-hydroxyethyl methacrylate (HEMA), polyalkenoic acid, biphenyl dimethacrylate (BPDM), biphenyl diacrylate (BPDA) and glycerol phosphate dimethacrylate (GPDM).

In consideration of the amount relationship with the monomer and oligomer, the filler is preferably included in an amount of 60 to 88 wt % based on the total weight of the paste composition, and the filler may include an inorganic filler, an organic filler, a stabilizer, etc.

The filler may include at least one selected from among an inorganic filler and an organic filler.

The inorganic filler may include at least one selected from among synthetic amorphous silica, crystalline silica, barium silicate, barium borosilicate, barium fluoroaluminoborosilicate, barium aluminoborosilicate, strontium silicate, strontium borosilicate, strontium aluminoborosilicate, calcium silicate, aluminosilicate, silicon nitride, titanium dioxide, calcium hydroxyapatite, zirconia and bioactive glass, and may be included in an amount of 60 to 88 wt % based on the total weight of the paste composition.

Here, synthetic amorphous silica, crystalline silica and zirconia may be in the form of particles, and the average diameter of the particles may be 0.01 to 0.1 μm, and the amount thereof may be 1 to 15 wt %. If the amount thereof is less than 1 wt %, the density of the filler in the paste may decrease. On the other hand, if the amount thereof exceeds 15 wt %, the viscosity may increase, making it difficult to mix a large amount of filler therein.

Typically, the inorganic filler is hydrophilic, and thus miscibility with the hydrophobic methacrylate or acrylate monomer is poor, so a binder component may be included, or the inorganic filler may be surface-treated with a silane-coupling agent, thereby increasing affinity to the monomer.

Also, barium silicate, barium borosilicate, barium fluoroaluminoborosilicate, barium aluminoborosilicate, strontium silicate, strontium borosilicate and strontium aluminoborosilicate may be in the form of particles, and the average diameter of the particles may be 0.1 to 3 μm. If the average diameter of the particles is less than 0.1 μm, uniform dispersion thereof in the paste composition may become difficult due to cohesion between particles, and removal of bubbles and processing may become difficult due to the increased viscosity. On the other hand, if the average diameter of the particles exceeds 3 μm, bonding strength and properties may be deteriorated, and after application to the tooth, large particles may be lost therefrom when the tooth wears, and the luster thereof may thus be reduced.

The amount of the inorganic filler having an average particle diameter of 0.1 to 3 μm may be 65 to 84 wt %, which may affect hardness and properties. If the amount thereof is less than 65 wt %, low flexural strength, making it difficult to repair the posterior teeth, may result. On the other hand, if the amount thereof exceeds 84 wt %, it is difficult to mix the monomer and the filler.

The organic filler may be subjected to bulk polymerization, emulsion polymerization, suspension polymerization or the like together with the monomer containing the unsaturated double bond or a monomer compatible therewith, and may thus be manufactured in the form of a powder, whereby particles having an average diameter of 0.005 to 100 μm may be used. In some cases, mechanical strength may be increased by increasing the molecular weight of the monomer containing the unsaturated double bond to be cured, rather than adding the inorganic or organic filler.

The particles used for the paste composition may have an average particle diameter of 0.01 to 3 μm, preferably 0.1 to 2 μm. When using particles having a size greater than 3 μm, tool wear and processing time during CAM processing may increase, and surface polishing may become difficult. On the other hand, when using particles having a size less than 0.01 μm, the viscosity of the blank composition may increase, making it difficult to remove bubbles and to process the composite blank.

The stabilizer preferably includes a phenolic stabilizer, a phosphate stabilizer or the like.

The paste composition may be added with other known compounds within a range that does not impede the effects of the invention. Therefore, a polymerization inhibitor, an antioxidant, a colorant, a fluorescent agent, a fluorine additive, a stabilizer, and the like may be added.

The polymerization reaction of the paste composition may be performed in a cation formation mechanism, an anion formation mechanism, a radical formation mechanism, etc., depending on the type of catalyst used for the reaction, and the radical formation mechanism is most preferable.

Depending on the polymerization reaction mechanism, the polymerization reaction may be carried out through a photopolymerization reaction or a thermal polymerization reaction. Accordingly, the polymerization initiator may include at least one selected from among a photopolymerization initiator and a thermal polymerization initiator, and preferably, a thermal polymerization initiator is used.

In the thermal polymerization reaction, a radical may be formed by heat to thereby initiate polymerization, and the thermal polymerization initiator may be a peroxide initiator such as benzoyl peroxide.

The polymerization initiator for such a polymerization reaction may be included in the composition within a range that does not affect the properties of the product while inducing a polymerization reaction, and may vary depending on the types and amounts of other components of the composition and the type of catalyst.

The composite paste may include 100 parts by weight of the unsaturated-double-bond compound, 50 to 1,000 parts by weight of the filler, and 0.01 to 5 parts by weight of the polymerization initiator.

The composite paste may have consistency of 5 to 70 mm. If the consistency is less than 5 mm, the amount of the filler relative to that of the monomer is too high, and thus defects may remain even after pressurization of the composite paste, undesirably deteriorating flexural strength when curing the composite paste. On the other hand, if the consistency exceeds 70 mm, the amount of the filler relative to that of the monomer is too low and thus the flexural strength of the monomer may remain evident after curing the composite paste, which is undesirable.

In addition, the present invention pertains to a dental composite blank manufactured by polymerizing a composite paste including 100 parts by weight of at least one unsaturated-double-bond compound selected from the group consisting of a monomer containing an unsaturated double bond and an oligomer of a monomer containing an unsaturated double bond, 50 to 1,000 parts by weight of a filler, and 0.01 to 5 parts by weight of a polymerization initiator, in which the composite blank has flexural strength of 200 to 300 MPa, preferably 210 to 300 MPa, and more preferably 210 to 260 MPa.

MODE FOR INVENTION

Examples

Preparation Example 1: Preparation of First Dental Composite Paste

Bis-GMA (2,2-bis-(4-(2-hydroxy-3-methacryloyloxy-propoxy)phenyl)propane), TEGDMA (triethylene glycol dimethacrylate), BPO (benzoyl peroxide), barium silicate, and silica were mixed at a weight ratio of 9.4:14.2:0.4:70:6 (wt %).

Specifically, Bis-GMA and TEGDMA, serving as monomers, and BPO, serving as an initiator, were mixed at the above weight ratio using a mixer at a predetermined rate, and as fillers, barium silicate and silica at the above weight ratio were added 3 to 5 times in divided amounts, thereby preparing a first dental composite paste.

Preparation Examples 2 to 5: Preparation of Second to Fifth Dental Composite Pastes The components for the monomer, initiator and filler were added in the amounts shown in Table 1 below, thereby preparing second to fifth dental composite pastes.

The consistency of the first to fifth dental composite pastes was measured in a manner in which 1.0 g of each of the first to fifth dental composite pastes was extruded on a glass, cautiously covered with another glass, and pressed for 60 sec using a loading device at 150 N, and after 60 sec, the loading device and the glass were removed, after which the lengths of the long side and the short side of the spread paste were measured, and the average value thereof was taken as the consistency (mm). The results thereof are shown in Table 1 below.

TABLE 1

| Classification | | Composition | | Consistency |
| --- | --- | --- | --- | --- |
| | | Component | Mass % | (mm) |
| Preparation Example 1 | Monomer | Bis-GMA (2,2-bis-(4-(2-hydroxy-3-methacryloyloxypropoxy)phenyl)propane) | 9.4 | 34.5 |
| | | TEGDMA (triethylene glycol dimethacrylate) | 14.2 | |
| | Initiator | BPO (benzoyl peroxide) | 0.4 | |
| | Filler | Barium silicate (average particle size: 0.7 μm) | 70 | |
| | | Silica (average particle size: 12 nm) | 6 | |
| Preparation Example 2 | Monomer | UDMA (urethane dimethacrylate) | 6 | 14.2 |
| | | TEGDMA (triethylene glycol dimethacrylate) | 13.6 | |
| | Initiator | BPO (benzoyl peroxide) | 0.4 | |
| | Filler | Barium silicate (average particle size: 0.4 μm) | 70 | |
| | | Silica (average particle size: 10 nm) | 10 | |
| Preparation Example 3 | Monomer | UDMA (urethane dimethacrylate) | 8 | 14.6 |
| | | TEGDMA (triethylene glycol dimethacrylate) | 11.6 | |
| | Initiator | BPO (benzoyl peroxide) | 0.4 | |
| | Filler | Barium silicate (average particle size: 0.4 μm) | 70 | |
| | | Silica (average particle size: 10 nm) | 10 | |
| Preparation Example 4 | Monomer | UDMA (urethane dimethacrylate) | 8.8 | 21.6 |
| | | TEGDMA (triethylene glycol dimethacrylate) | 13.8 | |
| | Initiator | BPO (benzoyl peroxide) | 0.4 | |
| | Filler | Barium silicate (average particle size: 0.4 μm) | 68 | |
| | | Silica (average particle size: 10 nm) | 10 | |
| Preparation Example 5 | Monomer | Bis-GMA (2,2-bis-(4-(2-hydroxy-3-methacryloyloxypropoxy)phenyl)propane) | 9.4 | 90 |
| | | TEGDMA (triethylene glycol dimethacrylate) | 14.2 | |
| | Initiator | BPO (benzoyl peroxide) | 0.4 | |
| | Filler | Barium silicate (average particle size: 0.7 μm) | 0 | |
| | | Silica (average particle size: 12 nm) | 0 | |

Example 1: Manufacture of Dental Composite Blank

With reference to FIGS. 1a and 1b, a mold was obtained by cutting the inside of a nylon plate having a height of 18 mm and a width and a length of 20 mm×20 mm to form a quadrangular prism having a thickness of 5 mm, a width and a length of 15 mm×15 mm, and a height of 18 mm. The first dental composite paste, prepared in Preparation Example 1, was placed in the mold so that the inside of the mold was filled without gaps remaining. The mold filled with the first dental composite paste prepared in Preparation Example 1 was fixed in a HIP (Hot Isostatic Pressing) device.

Thereafter, the inner temperature of the HIP device was elevated to 55° C., after which pressurization to 40 MPa with nitrogen, maintenance thereof for 5 min, depressurization to 5 MPa and maintenance thereof for 1 min were repeated 9 times.

Next, the inner temperature of the HIP device was elevated to 120° C., the pressure was maintained at 40 MPa, and the first dental composite paste was cured for 2 hr. After 2 hr, the pressure was gradually decreased to atmospheric pressure, after which the resulting dental composite blank was obtained after being separated from the mold.

Example 2: Manufacture of Dental Composite Blank

The second dental composite paste prepared in Preparation Example 2 was placed in the mold so that the inside of the mold was filled without gaps remaining. The mold filled with the second dental composite paste prepared in Preparation Example 2 was fixed in a HIP (Hot Isostatic Pressing) device.

Thereafter, the inner temperature of the HIP device was elevated to 55° C., after which pressurization to 40 MPa with nitrogen, maintenance thereof for 5 min, depressurization to 5 MPa and maintenance thereof for 1 min were repeated 9 times.

Next, the inner temperature of the HIP device was elevated to 120° C., the pressure was maintained at 40 MPa, and the second dental composite paste was cured for 2 hr. After 2 hr, the pressure was gradually decreased to atmospheric pressure, after which the resulting dental composite blank was obtained after being separated from the mold.

Example 3: Manufacture of Dental Composite Blank

A dental composite blank was manufactured in the same manner as in Example 2, with the exception that the inner temperature of the HIP device was elevated to 55° C. and simultaneously, pressurization to 40 MPa with nitrogen was performed, and maintenance of the temperature and pressure for 5 min, depressurization to 5 MPa without changing the temperature, and maintenance thereof for 1 min were performed once, followed by 9 repetitions of pressurization and depressurization without any change in the temperature, rather than elevating the inner temperature of the HIP device to 55° C. and then repeating pressurization to 40 MPa with nitrogen, maintenance thereof for 5 min, depressurization to 5 MPa and maintenance thereof for 1 min 9 times, as in Example 2.

Example 4: Manufacture of Composite Blank

A dental composite blank was manufactured in the same manner as in Example 2, with the exception that the inner temperature of the HIP device was elevated to 90° C., rather than elevating the inner temperature of the HIP device to 55° C., as in Example 2.

Example 5: Manufacture of Dental Composite Blank

The third dental composite paste prepared in Preparation Example 3 was placed in the mold so that the inside of the mold was filled without gaps remaining. The mold filled with the third dental composite paste prepared in Preparation Example 3 was fixed in a HIP device.

Thereafter, the inner temperature of the HIP device was elevated to 55° C., after which pressurization to 20 MPa with nitrogen, maintenance thereof for 5 min, depressurization to 5 MPa and maintenance thereof for 1 min were repeated 9 times.

Next, the inner temperature of the HIP device was elevated to 120° C., the pressure was maintained at 20 MPa, and the third dental composite paste was cured for 2 hr. After 2 hr, the pressure was gradually decreased to atmospheric pressure, after which the resulting dental composite blank was obtained after being separated from the mold.

Example 6: Manufacture of Composite Blank

A dental composite blank was manufactured in the same manner as in Example 5, with the exception that pressurization to MPa with nitrogen, maintenance thereof for 5 min, depressurization to 5 MPa and maintenance thereof for 1 min were performed once, rather than repeating pressurization to 20 MPa with Nitrogen, Maintenance Thereof for 5 Min, Depressurization to 5 MPa and maintenance thereof for 1 min 9 times, as in Example 5.

Example 7: Manufacture of Dental Composite Blank

A dental composite blank was manufactured in the same manner as in Example 1, with the exception that the fourth dental composite paste prepared in Preparation Example 4 was used in lieu of the first dental composite paste prepared in Preparation Example 1, and pressurization to 40 MPa with nitrogen, maintenance thereof for 5 min, depressurization to 5 MPa and maintenance thereof for 1 min were repeated 3 times, rather than repeating pressurization to 40 MPa with nitrogen, maintenance thereof for 5 min, depressurization to 5 MPa and maintenance thereof for 1 min 9 times, as in Example 1.

Example 8: Manufacture of Composite Blank

A dental composite blank was manufactured in the same manner as in Example 7, with the exception that pressurization to 40 MPa with air, maintenance thereof for 5 min, depressurization to 5 MPa and maintenance thereof for 1 min were performed once, rather than repeating pressurization to 40 MPa with nitrogen, maintenance thereof for 5 min, depressurization to 5 MPa and maintenance thereof for 1 min 3 times, as in Example 7.

Comparative Example 1: Manufacture of Composite Blank

A dental composite blank was manufactured in the same manner as in Example 1, with the exception that the inner temperature of the HIP device was elevated to 60° C., after which the step of repeating pressurization to 40 MPa with nitrogen, maintenance thereof for 5 min, depressurization to 5 MPa and maintenance thereof for 1 min 9 times, as in Example 1, was not performed.

Comparative Example 2: Manufacture of Composite Blank

A dental composite blank was manufactured in the same manner as in Example 1, with the exception that pressurization to 1 MPa with nitrogen, maintenance thereof for 5 min, depressurization to 1 MPa and maintenance thereof for 1 min were performed once, and the composite paste was then cured for 2 hr at a pressure of 1 MPa, rather than repeating pressurization to MPa with nitrogen, maintenance thereof for 5 min, depressurization to 5 MPa and maintenance thereof for 1 min 9 times, followed by curing the composite paste for 2 hr at a pressure of 40 MPa, as in Example 1.

Comparative Example 3: Manufacture of Composite Blank

A composite blank was manufactured in the same manner as in Example 1, with the exception that the fifth dental composite paste prepared in Preparation Example 5 was used in lieu of the first dental composite paste prepared in Preparation Example 1, and pressurization to 1 MPa with nitrogen, maintenance thereof for 5 min, depressurization to 1 MPa and maintenance thereof for 1 min were performed once, and the composite paste was then cured for 2 hr at a pressure of 1 MPa, rather than repeating pressurization to 40 MPa with nitrogen, maintenance thereof for 5 min, depressurization to 5 MPa and maintenance thereof for 1 min 9 times, followed by curing the composite paste for 2 hr at a pressure of 40 MPa, as in Example 1.

The main conditions of Examples 1 to 8 and Comparative Examples 1 to 3 are summarized in Table 2 below.

TABLE 2

| | | Process before curing | | | | | |
|---|---|---|---|---|---|---|---|
| | Paste used | Pressurization | Depressurization | Repetition number | Temperature | Gas | Pressure upon curing |
| Example 1 | Preparation Example 1 | 40 MPa | 5 MPa | 9 | 55° C. | Nitrogen | 40 MPa |
| Example 2 | Preparation Example 2 | 40 MPa | 5 MPa | 9 | 55° C. | Nitrogen | 40 MPa |
| Example 3 | Preparation Example 2 | 40 MPa | 5 MPa | 9 | 55° C. | Nitrogen | 40 MPa |

TABLE 2-continued

| | | Process before curing | | | | | |
|---|---|---|---|---|---|---|---|
| | Paste used | Pressurization | Depressurization | Repetition number | Temperature | Gas | Pressure upon curing |
| Example 4 | Preparation Example 2 | 40 MPa | 5 MPa | 9 | 90° C. | Nitrogen | 40 MPa |
| Example 5 | Preparation Example 3 | 20 MPa | 5 MPa | 9 | 55° C. | Nitrogen | 20 MPa |
| Example 6 | Preparation Example 3 | 20 MPa | 5 MPa | 1 | 55° C. | Nitrogen | 20 MPa |
| Example 7 | Preparation Example 4 | 40 MPa | 5 MPa | 3 | 55° C. | Nitrogen | 40 MPa |
| Example 8 | Preparation Example 4 | 40 MPa | 5 MPa | 1 | 55° C. | Air | 40 MPa |
| Comparative Example 1 | Preparation Example 1 | — | — | — | — | — | 40 MPa |
| Comparative Example 2 | Preparation Example 1 | 1 MPa | 1 MPa | 1 | 55° C. | Nitrogen | 1 MPa |
| Comparative Example 3 | Preparation Example 5 | 1 MPa | 1 MPa | 1 | 55° C. | Nitrogen | 1 MPa |

TEST EXAMPLES

Test Example 1: Measurement of Cracks or Bubbles and Flexural Strength of Dental Composite Blank The composite blank manufactured in each of Examples 1 to 8 and Comparative Examples 1 to 3 was processed to a thickness of 1.2 mm±0.2 mm, a width of 4.0 mm±0.2 mm, and a length of 14 mm or more, the surface thereof was polished with No. 2000 abrasive paper, and a 3-point bending test was conducted under the conditions of an interpoint distance of 12 mm and a crosshead speed of 1.0 mm/min.

Also, the composite blank manufactured in each of Examples 1 to 8 and Comparative Examples 1 to 3 was sliced with a thickness of 1 mm to afford 10 plates, which were then observed at 10× magnification with a loupe, and the presence or absence of cracks or bubbles was observed.

The test results thereof are shown in Table 3 below.

TABLE 3

| No. | Cracks | Bubbles | Flexural strength |
|---|---|---|---|
| Example 1 | Not found | Not found | 210 MPa |
| Example 2 | Not found | Not found | 256 MPa |
| Example 3 | Not found | Not found | 249 MPa |
| Example 4 | Cracked | Bubbled | — (not measured due to bubbles) |
| Example 5 | Not found | Not found | 222 MPa |
| Example 6 | Not found | Not found | 195 MPa |
| Example 7 | Not found | Not found | 242 MPa |
| Example 8 | Cracked | Not found | 198 MPa |
| Comparative Example 1 | Cracked | Not found | 183 MPa |
| Comparative Example 2 | Cracked | Bubbled | — (not measured due to bubbles) |
| Comparative Example 3 | Not found | Not found | 122 MPa |

As is apparent from Table 3, neither cracks nor bubbles were observed in the dental composite blanks manufactured in Examples 1 to 3 and 5 to 8, unlike the dental composite blanks manufactured in Comparative Examples 1 to 3, the flexural strength thereof was evaluated to be higher, and the properties of the dental composite blank manufactured in Example 2 were regarded as the best.

Also, the flexural strength could not be measured in the dental composite blanks manufactured in Example 4 and Comparative Example 2 due to the bubbles in the blank.

Therefore, it can be confirmed for the dental composite blank of the present invention that bubbles and cracks were not generated by repeatedly performing pressurization and depressurization in the appropriate temperature range before curing the dental composite paste. Also, the flexural strength of the dental composite blanks manufactured in Examples 1 to 3 and 5 to 8 was high compared to the dental composite blanks manufactured in Comparative Examples 1 to 3, based on which the mechanical properties were evaluated to be improved.

The scope of the invention is represented by the claims below rather than the aforementioned detailed description, and all changes or modified forms that are capable of being derived from the meaning, range, and equivalent concepts of the appended claims should be construed as being included in the scope of the present invention.

INDUSTRIAL APPLICABILITY

According to the present invention, a dental composite blank and a method of manufacturing the same are effective at dispersing a non-dispersed filler and removing bubbles by repeating pressurization at different pressures before curing a dental composite paste.

In addition, according to the present invention, a dental composite blank and a method of manufacturing the same are effective at improving mechanical properties by dispersing a non-dispersed filler and removing bubbles.

The invention claimed is:

1. A method of manufacturing a dental composite blank, comprising:
    (a) placing a composite paste in a mold;
    (b) pressurizing the composite paste placed in the mold at a first pressure ($P_1$);
    (c) pressurizing the composite paste placed in the mold at a second pressure ($P_2$); and
    (d) curing the pressurized composite paste,
    wherein,
    each of steps (b) and (c) is performed once or multiple times,
    the first pressure ($P_1$) is less than or greater than the second pressure ($P_2$), and
    any one of the first pressure ($P_1$) and the second pressure ($P_2$) is 5 to 300 MPa and a remaining one thereof is 1 to 10 MPa.

2. The method of claim 1, wherein steps (b) and (c) are repeatedly performed.

3. The method of claim 1, wherein each of steps (b) and (c) is performed 1 to 20 times, and steps (b) and (c) are alternately performed.

4. The method of claim 1, wherein a difference between the first pressure ($P_1$) and the second pressure ($P_2$) is 5 to 299 MPa.

5. The method of claim 1, wherein steps (b) and (c) are each independently performed at 10 to 59° C.

6. The method of claim 1, wherein curing is not performed in each of steps (b) and (c).

7. The method of claim 1, wherein steps (b) and (c) are performed in an inert gas atmosphere.

8. The method of claim 1, wherein step (d) is performed at a pressure of 5 to 300 MPa.

9. The method of claim 8, wherein step (d) is performed at a temperature of 80 to 200° C.

10. The method of claim 1, wherein step (b) is performed multiple times, and
during step (b) performed multiple times, a pressure ($P_1(1)$) in step (b) performed for a first time is same as or different from a pressure ($P_1(2)$) in step (b) performed later.

11. The method of claim 1, wherein step (c) is performed multiple times, and
during step (c) performed multiple times, a pressure ($P_2(1)$) in step (c) performed for a first time is same as or different from a pressure ($P_2(2)$) in step (c) performed later.

12. The method of claim 1, wherein the composite paste comprises at least one unsaturated-double-bond compound selected from among a monomer containing an unsaturated double bond and an oligomer of a monomer containing an unsaturated double bond; a filler; and a polymerization initiator.

13. The method of claim 12, wherein the monomer comprises at least one selected from the group consisting of 2,2-bis[4-(2-hydroxy-3-methacryloxypropoxy) phenyl]propane (Bis-GMA), ethylene glycol dimethacrylate (EGDMA), ethylene glycol diacrylate (EDGA), triethylene glycol dimethacrylate (TEGDMA), triethylene glycol diacrylate (TEGDA), ethoxylated bisphenol A dimethacrylate (Bis-EMA), urethane dimethacrylate (UDMA), polyurethane diacrylate (PUDA), dipentaerythritol pentaacrylate monophosphate (PENTA), 2-hydroxyethyl methacrylate (HEMA), polyalkenoic acid, biphenyl dimethacrylate (BPDM), biphenyl diacrylate (BPDA) and glycerol phosphate dimethacrylate (GPDM).

14. The method of claim 12, wherein the filler comprises at least one selected from among an inorganic filler and an organic filler, and
the inorganic filler comprises at least one selected from the group consisting of synthetic amorphous silica, crystalline silica, barium silicate, barium borosilicate, barium fluoroaluminoborosilicate, barium aluminoborosilicate, strontium silicate, strontium borosilicate, strontium aluminoborosilicate, calcium silicate, aluminosilicate, silicon nitride, titanium dioxide, calcium hydroxyapatite, zirconia and bioactive glass.

15. The method of claim 12, wherein the polymerization initiator comprises a thermal polymerization initiator.

16. The method of claim 12, wherein the composite paste comprises 100 parts by weight of the unsaturated-double-bond compound; 50 to 1,000 parts by weight of the filler; and 0.01 to 5 parts by weight of the polymerization initiator.

17. The method of claim 1,
wherein,
each of steps (b) and (c) is performed 1 to 20 times, and steps (b) and (c) are performed alternately,
two consecutive first pressures are different,
two consecutive second pressures are different, and
the curing is performed at a pressure higher than the first pressure and the second pressure of the last repeat step.

* * * * *